United States Patent
Xu et al.

(10) Patent No.: US 11,260,004 B2
(45) Date of Patent: Mar. 1, 2022

(54) ORAL CARE COMPOSITION

(71) Applicant: COLGATE-PALMOLIVE COMPANY, New York, NY (US)

(72) Inventors: Shao Peng Xu, Guangzhou (CN); Dai Lin Chen, Guangzhou (CN); Neelima Utgikar, Dombivli (IN)

(73) Assignee: Colgate-Palmolive Company, New York, NY (US)

( * ) Notice: Subject to any disclaimer, the term of this patent is extended or adjusted under 35 U.S.C. 154(b) by 3 days.

(21) Appl. No.: 16/428,474

(22) Filed: May 31, 2019

(65) Prior Publication Data

US 2020/0375859 A1  Dec. 3, 2020

(51) Int. Cl.
*A61K 8/34* (2006.01)
*A61Q 11/00* (2006.01)
*A61K 8/63* (2006.01)

(52) U.S. Cl.
CPC .............. *A61K 8/347* (2013.01); *A61K 8/63* (2013.01); *A61Q 11/00* (2013.01)

(58) Field of Classification Search
CPC . A61Q 11/00; A61K 8/36; A61K 8/63; A61K 8/347
See application file for complete search history.

(56) References Cited

U.S. PATENT DOCUMENTS

| 8,263,048 B2 * | 9/2012 | Yang | .............. A61K 8/88 424/57 |
|---|---|---|---|
| 2009/0087501 A1 | 4/2009 | Cummins | |
| 2012/0244085 A1 | 9/2012 | Trivedi et al. | |
| 2013/0045954 A1 | 2/2013 | De Leij et al. | |
| 2019/0167555 A1 | 6/2019 | Ku | |

FOREIGN PATENT DOCUMENTS

WO   2019/108215   6/2019

OTHER PUBLICATIONS

Ananjiwala Sheetal et al., 2006, "Quantification of eugenol, luteolin, ursolic acid, and oleanolic acid in black (Krishna tulasi) and green (Sri tulasi) varieties of Ocimum sanctum Linn. using high-performance thin-layer chromatography," Journal of AOAC International 89(6):1467-1474.

Devanand Gupta et al., 2014, "A randomized controlled clinical trial of Ocimum sanctum and chlorhexidine mouthwash on dental plaque and gingival inflammation," Journal of Ayurveda and Integrative Medicine 5(2):109-116.

International Search Report and Written Opinion of the International Searching Authority in International Application PCT/US2019/034986, dated Jul. 25, 2019.

* cited by examiner

*Primary Examiner* — Lezah Roberts

(57) ABSTRACT

An oral care composition, including a mixture of antibacterial agents, the mixture of antibacterial agents including oleanic acid and eugenol at a 2:1 to 3:1 weight ratio.

3 Claims, No Drawings

ORAL CARE COMPOSITION

BACKGROUND

Gum bleeding is associated with many common oral conditions, such as gingivitis. Gum bleeding may be caused by a buildup of plaque, a soft, sticky, colorless film of bacteria that forms on the teeth and gums, and produces toxins that may inflame or infect the gum tissue to cause gingivitis. Gingivitis is the initial stage of gum disease and, if left untreated, may cause periodontitis.

Among other uses, antibacterial agents have been used in oral care products to reduce plaque and gingivitis, and hence reduce gum bleeding. However, the antibacterial efficacy of compounds may be affected by other active ingredients in the oral care product, or by limits on the amounts of an antibacterial agent that can be used.

Accordingly, it would be useful to develop oral care compositions, such as toothpastes and mouthwashes, configured to provide improved antibacterial efficacy. Additionally, it would be useful to develop oral care composition with natural or botanically-based active ingredients.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing an oral care composition, including from 0.04 weight % to 2.80 weight % of a mixture of antibacterial agents, based on a total weight of the oral care composition, wherein the mixture of antibacterial agents includes oleanic acid and eugenol at a 2:1 to 3:1 weight ratio.

Eugenol may include one or more of eugenol, methyl eugenol, iso-eugenol, or mixtures thereof.

The oral care composition may include from 0.10 weight % to 1.0 weight % of the mixture of antibacterial agents.

The mixture of antibacterial agents may include oleanic acid and eugenol at a 2:1 weight ratio.

The mixture of antibacterial agents may consist essentially of oleanic acid and eugenol at a 2:1 weight ratio.

The oral care composition may include from 0.02 weight % to 2.0 weight % of oleanic acid, based on the total weight of the oral care composition; and from 0.01 weight % to 1.0 weight % of eugenol, based on the total weight of the oral care composition.

The oral care composition may include from 0.05 weight % to 0.50 weight % of oleanic acid; and from 0.025 weight % to 0.25 weight % of eugenol.

The oral care composition may include 0.10 weight % of oleanic acid; and 0.05 weight % of eugenol.

Other than the mixture of antibacterial agents, the oral care composition may lack another antibacterial agent.

The foregoing and/or other aspects and utilities embodied in the present disclosure may also be achieved by providing a method for increasing the antibacterial effect of an oral care composition, including adding a mixture of antibacterial agents to the oral care composition, wherein the mixture of antibacterial agents includes oleanic acid and eugenol at a 2:1 to 3:1 weight ratio.

Eugenol may include one or more of eugenol, methyl eugenol, iso-eugenol, or mixtures thereof.

The mixture of antibacterial agents may include oleanic acid and eugenol at a 2:1 weight ratio.

The mixture of antibacterial agents may consist essentially of oleanic acid and eugenol at a 2:1 weight ratio.

Other than the mixture of antibacterial agents, the oral care composition may lack another antibacterial agent.

DETAILED DESCRIPTION

Reference will now be made in detail to the various embodiments in the present disclosure. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. Phrases such as "in an embodiment," "in certain embodiments," and "in some embodiments" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, components, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some embodiments, some operations in the procedures, methods, techniques, and workflows disclosed herein may be combined and/or the order of some operations may be changed.

The inventors have surprisingly discovered a new, synergistic, mixture of antibacterial agents that lead to improve antibacterial efficacy. An oral care composition as disclosed herein includes a mixture of antibacterial agents. The mixture of antibacterial agents provides an improved antibacterial effect. The mixture of antibacterial agents includes oleanic acid and eugenol. In particular, the mixture of antibacterial agents includes oleanic acid and eugenol at a 2:1 to 3:1 ratio by weight. For example, the mixture of antibacterial agents may include oleanic acid and eugenol at a 2:1 ratio by weight.

In some embodiments, the mixture of antibacterial agents consists essentially of oleanic acid and eugenol. For example, the mixture of antibacterial agents may consist essentially of oleanic acid and eugenol at a 2:1 to 3:1 ratio by weight. For example, the mixture of antibacterial agents may consist essentially of oleanic acid and eugenol at a 2:1 ratio by weight.

In some embodiments, the mixture of antibacterial agents is derived from or based upon compounds or extracts isolated from plants.

Formula 1 illustrates a chemical structure of oleanic acid. Oleanic or oleanolic acid (3β-hydroxy-olea-12-en-28-oic) is a pentacyclic triterpenoid that is widely distributed in plants. For example, oleanic acid may be extracted from a number of medicinal plants, such as *Calendula officinalis* L. (marigold), *Ligustrum lucidum* Ait (oleaceae), and *Hemsleya Chinensis* Cogn.

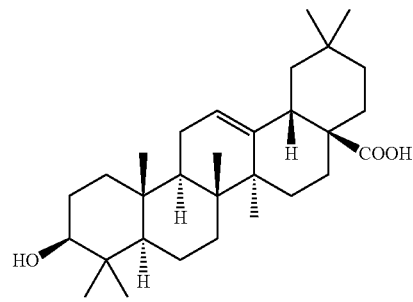

Formula 1

Formula 2 illustrates a chemical structure of eugenol. Eugenol (4-allyl-2-methoxyphenol), is a naturally occurring phenol essential oil extracted from, for example, cloves, nutmeg, cinnamon, basil, and bay leaf. Eugenol may also be provided as methyl eugenol or iso-eugenol.

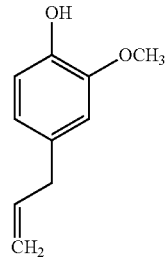

Formula 2

As described above, the inventors have surprisingly discovered that the combination of oleanic acid and eugenol has increased antibacterial effects. In some embodiments, the antibacterial effects of oleanic acid combined with eugenol are greater than those of oleanic acid or eugenol separately. In other embodiments, the antibacterial effects of oleanic acid combined with eugenol at a 2:1 ratio are greater than those of oleanic acid combined with eugenol at other ratios, such as 3:1 or greater.

In certain embodiments, the mixture of antibacterial agents including oleanic acid and eugenol is the only antibacterial agent present in the oral care composition. In other embodiments, the oral care composition includes no other antibacterial agents apart from the mixture of antibacterial agents.

In certain embodiments, the oral care composition includes from about 0.04 weight % to about 2.8 weight % mixture of antibacterial agents, based on the total weight of the oral care composition. For example, the oral care composition includes from about 0.05 weight % to about 2.0 weight % mixture of antibacterial agents, from about 0.1 weight % to about 1 weight % mixture of antibacterial agents, or from about 0.1 weight % to about 0.5 weight % mixture of antibacterial agents, based on the total weight of the oral care composition. In one implementation, the oral care composition includes about 0.15 weight % mixture of antibacterial agents.

As described above, the mixture of antibacterial agents includes oleanic acid and eugenol. Eugenol may also be provided as eugenol, methyl eugenol, iso-eugenol, or combinations thereof. The mixture of antibacterial agents includes oleanic acid and eugenol at a 2:1 ratio by weight. In some embodiments, the mixture of antibacterial agents may include additional antibacterial agents. In other embodiments, the mixture of antibacterial agents only includes oleanic acid and eugenol.

For example, the oral care composition may include from about 0.02 weight % to about 2.0 weight %, from about 0.05 weight % to about 0.5 weight %, from about 0.1 weight % to about 0.25 weight %, or from about 0.1 weight % to about 0.2 weight % oleanic acid, based on the total weight of the oral care composition. In one preferred embodiment, the oral care composition may include 0.10 weight % oleanic acid. Correspondingly, the oral care composition may include from 0.01 weight % to 1.0 weight % eugenol, based on the total weight of the oral care composition. For example, the oral care composition includes from about 0.025 weight % to about 0.25 weight %, from about 0.02 weight % to about 0.6 weight %, from about 0.04 weight % to about 0.2 weight %, or from about 0.05 weight % to about 0.10 weight % eugenol, based on the total weight of the oral care composition. In a preferred embodiment, the oral care composition may include 0.05 weight % eugenol. In some embodiments, the oral care composition may include methyl eugenol and/or iso eugenol instead of or in addition to eugenol.

Generally, viscosity is an important parameter for oral care compositions, such as toothpastes or whitening gels. For example, when the viscosity of an oral care composition is too low, it may become too runny and physical phase separation may take place. In some cases, this will not only affect the aesthetics of the oral care composition but also the homogeneity of the ingredients in the oral care composition. On the other hand, if the viscosity of the oral care compositions is too high, the oral care composition will be difficult to manufacture and package. In addition, oral care compositions with high viscosity are very difficult for users to evacuate from commonly used packages, such as tubes or syringes. Accordingly, it's important to select ingredients for oral care compositions that achieve a desirable range of viscosity to ensure product manufacturability, stability, and quality, as well as consumer acceptance.

In some embodiments, the viscosity of the oral care composition is from about 10,000 centipoise (cPs) to about 500,000 cPs at 25° C. For example, the viscosity of the oral care composition is from about 50,000 cPs to about 400,000 cPs at 25° C. In one embodiment, the viscosity of the oral care composition is from about 125,000 cPs to about 300,000 cPs at 25° C.

In some embodiments, the oral care composition may include additional ingredients common to oral care compositions, such as carriers, dispersants, whitening agents, flavoring agents, tartar control agents, surfactants, sweeteners, humectants, colorants, antibacterial agents, preservatives, dyes, and pigments.

All ingredients used in the compositions described herein should be orally acceptable. "Orally acceptable" means an ingredient which is present in the composition as described in an amount and form which does not render the composition unsafe, unpalatable, or otherwise unsuitable for use in the oral cavity. In addition, the additional ingredients should not substantially inhibit the efficacy of the mixture of antibacterial agents described above.

In various embodiments of the present disclosure, the oral care composition includes an orally acceptable carrier. As used herein, an "orally acceptable carrier" refers to a material or combination of materials that are safe for use in the oral care compositions of the present disclosure while retaining significant efficacy for the mixture of antibacterial agents. In certain embodiments, the carrier is specifically selected to ensure that there is no substantially reduction in efficacy for the mixture of antibacterial agents. For example, the oral care composition may use water as the carrier. In certain embodiments, the oral care composition includes 90 weight % or less, 70 weight % or less, or 50 weight % or less carrier, based on the total weight of the oral care composition.

In certain embodiments, the oral care composition may include one or more humectants. In some embodiments, the humectant is a mixture of humectants, such as glycerin and sorbitol, and a polyhydric alcohol, such as propylene glycol, butylene glycol, hexylene glycol, polyethylene glycol. In certain embodiments, the oral care composition includes from 5 weight % to 40 weight % or from 10 weight % to 30 weight % humectant, based on a total weight of the oral care composition.

The oral care composition may include one or more whitening agent. As used herein, a "whitening agent" is a material that affects whitening of a tooth surface to which it is applied. For example, in some embodiments, the whitening agent is an oxidizing agent. In its broadest sense, "oxidizing agent" is intended to include those compounds which can accept an electron from another molecule in the environment of the oral cavity without having a deleterious or unacceptably harmful effect on the oral cavity in normal and accepted use.

In some embodiments, the whitening agent may include peroxides and hydroperoxides, such as hydrogen peroxide, peroxides of alkali and alkaline earth metals, organic peroxy compounds, peroxy acids, salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as percarbonate, perphosphate, perborate and persilicate salts of alkali and alkaline earth metals such as lithium, potassium, sodium, magnesium, calcium and barium, and mixtures thereof. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite.

In some embodiments, the oral care composition includes from about 0.01% to about 50% whitening agent based on a total weight of the oral care composition. For example, the oral care composition includes from about 0.05 weight % to about 40 weight % whitening agent. In one embodiment, the oral care composition includes about 0.1 weight % whitening agent based on a total weight of the oral care composition.

In one embodiment, the oral care composition includes one or more surfactants. In some embodiments, the surfactants enhance stability of the composition, help clean the oral cavity surfaces through detergency, and provide foam upon agitation, e.g., during brushing with an oral care composition of the disclosure. Surfactants or surface active agents generally achieve increased whitening action by thoroughly dispersing the whitening agent throughout the oral cavity. In various embodiments, suitable surface active agents may function as a surface active agent, emulsifier, and/or foam modulator.

Any orally acceptable surfactant, most of which are anionic, nonionic, cationic, or amphoteric, may be used. A combination of surfactants may also be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate, and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, the oral care composition includes from about 0.01% to about 20.0% surfactant based on a total weight of the oral care composition. For example, the oral care composition includes from about 1.0 weight % to about 10.0 weight % surfactant. In one embodiment, the oral care composition includes about 2 weight % surfactant based on a total weight of the oral care composition. For example, the oral care composition may include about 2 weight % sodium lauryl sulfate.

In certain embodiments, the oral care composition may include thickening agents or thickeners. Any orally acceptable thickening agent may be used, including without limitation carbomers, also known as carboxyvinyl polymers, carrageenans, also known as Irish moss and more particularly carrageenan (iota-carrageenan), high molecular weight polyethylene glycols (such as CARBOWAX™, available from The Dow Chemical Company), cellulosic polymers such as hydroxyethylcellulose, carboxymethylcellulose ("CMC") and salts thereof, e.g., CMC sodium, natural gums such as karaya, xanthan, gum arabic and tragacanth, colloidal magnesium aluminum silicate, and colloidal or fumed silica and mixtures of the same. The thickening agent may be a combination of one or more orally acceptable thickening agents.

In some embodiments, the oral care composition includes from about 0.01% to about 30% thickening agent based on a total weight of the oral care composition. For example, the oral care composition includes from about 0.1 weight % to about 20 weight % thickening agent. In yet another example, the oral care composition includes from about 0.5 weight % to about 10 weight % thickening agent based on a total weight of the oral care composition. For example, the oral care composition may include about 3 weight % fumed silica.

In some embodiments, the oral care composition includes an antioxidant. Acceptable antioxidants include BHA, BHT, vitamin A, carotenoids, vitamin E, flavonoids, polyphenols, ascorbic acid, herbal antioxidants, chlorophyll, melatonin and mixtures thereof. In some embodiments, the oral care composition includes from about 0.001% to about 1% antioxidants based on a total weight of the oral care composition. In one embodiment, the oral care composition includes about 0.03 weight % antioxidant by weight.

In certain embodiments, the oral care composition includes one or more flavoring agents. Useful flavoring agents include any material or mixture of materials operable to enhance the taste of the oral care composition. Any orally acceptable natural or synthetic flavoring agent may be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some embodiments, the oral care composition includes from about 0.01% to about 5% flavoring agents based on a total weight of the oral care composition. For example, the oral care composition includes from about 0.05 weight % to about 3 weight % flavoring agents. In yet another embodiment, the oral care composition includes from about 0.1 weight % to about 3 weight %, from about 0.2 weight % to about 2.5 weight %, or about 1.5 weight % flavoring agents based on a total weight of the oral care composition. For example, the oral care composition may include about 1.5 weight % of dental cream flavor.

In some embodiments, the oral care composition may also include one or more sweeteners. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some embodiments may include one or more sweeteners. In some embodiments, the oral care composition includes from about 0.005% to about 5% sweeteners based on a total weight of the oral care composition. In other embodiments, the oral care composition includes from about 0.01% to about 1% sweeteners based on a total weight of the oral care composition. For example, the oral care composition may include about 0.5 weight % sodium saccharin and about 0.04 weight % sucralose.

In some embodiments, the oral care composition may include colorants. Colorants, such as dyes or pigments, may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants, if included, are present in very small quantities.

In some embodiments, the oral care composition may also include one or more pH modifying agents. The pH modifying agents among those useful herein include acidifying agents to lower pH, basifying agents to raise pH and buffering agents to control pH within a desired range. For example, one or more compounds selected from acidifying, basifying and buffering agents can be included to provide a pH of 2 to 10, or in various embodiments from about 2 to about 8, from about 3 to about 9, from about 4 to about 8, from about 5 to about 7, from about 6 to about 10, and from about 7 to about 9. Any orally acceptable pH modifying agent may be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range. In some embodiments, the oral care composition includes from about 0.01% to about 10% pH modifier agents based on a total weight of the oral care composition. For example, the oral care composition may include about 0.9 weight % sodium acid pyrophosphate (SAPP) and about 2 weight % tetrasodium pyrophosphate (TSPP) as a pH modifier.

The oral care composition may include one or more preservatives. In some embodiments, the preservatives improve an antimicrobial characteristic of the oral care composition to improve storage life or prevent decay.

In certain embodiments, the one or more preservatives include at least one of sodium benzoate, methyl paraben, ethyl paraben, zinc citrate, zinc oxide, triclosan, stannum salts, and combinations thereof.

The oral care composition may include an effective amount of preservatives. For example, the oral care composition may include an amount of preservatives effective to reduce a spoilage of the oral care composition during storage or use.

However, in some implementations, other than the mixture of antibacterial agents, the oral care composition lacks additional antibacterial agents or preservatives.

The oral care composition of the present disclosure may also include one or more additional active ingredients, which are operable for the prevention or treatment of a condition or disorder of hard or soft tissue of the oral cavity, the prevention or treatment of a physiological disorder or condition, or to provide a cosmetic benefit.

Some embodiments of the present disclosure include a dental abrasive or combination of dental abrasive agents. As used herein, the term "abrasive" or "abrasive agent" also includes materials commonly referred to as "polishing agents." Any orally acceptable abrasive may be used, but typically, type, fineness (particle size) and amount of abrasive should be selected so that tooth enamel is not excessively abraded in normal use of the composition. Suitable abrasives include without limitation silica (in the form of silica gel, hydrated silica or precipitated silica), alumina, insoluble phosphates, calcium carbonate, resinous abrasives such as urea-formaldehyde condensation products and the like.

Among insoluble phosphates useful as abrasives are orthophosphates, polymetaphosphates and pyrophosphates. Illustrative examples are dicalcium orthophosphate dihydrate, calcium pyrophosphate, n-calcium pyrophosphate, tricalcium phosphate, calcium polymetaphosphate and insoluble sodium polymetaphosphate.

Average particle size of an abrasive, if present, is generally from about 0.1 to 100 about μm. For example, the particle size may be from about 1 to about 80 μm or from about 5 to about 60 μm. In some embodiments, one or more abrasives are present in an amount of from about 0.01% to about 70% by weight, based on the total weight of the oral care composition. In other embodiments, the oral care composition includes from about 0.1 weight % to about 60 weight % abrasives. In some embodiments, the abrasive is calcium pyrophosphate. In some embodiments, the oral care composition includes from 0.01 weight % to about 70 weight % calcium pyrophosphate based on a total weight of the oral care composition. In another embodiment, the oral care composition includes about 20 weight % calcium pyrophosphate.

In various embodiments of the present disclosure, the oral care composition includes an anticalculus agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments, the anticalculus agent is present in an amount of from about 0.01% to about 30% weight based on the total weight of the oral care composition. In some embodiments, the oral care composition includes a mixture of anticalculus agents. In some embodiments, tetrasodium pyrophosphate (TSPP) and sodium tripolyphosphate (STPP) are used as the anticalculus agents. In some embodiments, the anticalculus agent includes from 0.1% to 10 weight % TSPP, or about 2 weight % TSPP.

The oral care compositions of the present disclosure may also include a synthetic anionic polymeric polycarboxylate. The synthetic anionic polymeric polycarboxylate may act as a stabilizer for the polyphosphate anti-tartar agent and may help to block access of painful or pain-causing materials, such as sugars, to the tooth nerves.

In some embodiments, the oral care composition optionally includes a source of fluoride ions. In some embodiments, the source of fluoride ions is selected from: fluoride, monofluorophosphate (MFP), and fluorosilicate salts. In some embodiments, one or more fluoride ion-releasing compounds are optionally present in an amount providing a total of 100 to 20,000 ppm, 200 to 5,000 ppm, or 500 to 2,500 ppm, fluoride ions. If present, in some embodiments, the amount of fluoride source in the oral care composition ranges from about 0.01% to about 10% by weight, based on the total weight of the oral care composition, typically about 0.5% to about 1.5 weight %. For example, the oral care composition may include about 0.76 weight % MFP.

The compositions also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. In some embodiments, one or more stannous ion sources are included in the oral care composition. For example, the oral care composition may include from about 0.01% to about 10% stannous ion source by weight, based on the total weight of the oral care composition. In one embodiment, the oral care composition includes from about 0.1 weight % to about 7 weight % stannous ion source or from about 0.2 weight % to about 5 weight % stannous ion source.

EXAMPLES

Aspects of the present disclosure may be further understood by referring to the following examples. The examples are illustrative, and are not intended to be limiting embodiments thereof. Table 1 illustrates an oral care composition according to embodiments of the present disclosure and three comparative examples. The compositions of Table 1 had the same amount for all ingredients except that Oral Care Composition Example 1 included both oleanic acid and eugenol at a 2:1 weight ratio, while Comparative Example A and Comparative Example B included only oleanic acid or eugenol, respectively. Comparative Example C included both oleanic acid and eugenol at a 3:1 weight ratio.

TABLE 1

| Ingredient | Oral Care Composition Example 1 | Comparative Example A | Comparative Example B | Comparative Example C |
|---|---|---|---|---|
| Oleanolic Acid | 0.1% | 0.1% | — | 0.15% |
| Eugenol | 0.05% | — | 0.05% | 0.05% |
| Humectant | | 31% | | |
| Thickener | | 1.0% | | |
| Abrasives | | 45% | | |
| Surfactants | | 2.55% | | |
| Sodium monofluorophosphate | | 1.1% | | |
| Tetra sodium pyrophosphate | | 1.1% | | |
| Water, flavor, sweetener and minors | q.s | q.s | q.s | q.s |

Table 2 illustrates an antibacterial efficacy of the oral care compositions. The antibacterial composition was measured under the University of Manchester (UoM) biofilm model as follows: dental plaque was collected from 4 healthy volunteers and pooled together as inoculum. The optical density (OD) of the inoculum was matched to 0.3 absorbance at 610 nm. Sterile HAP disks were incubated under anaerobic conditions at 37° C. for 24 hours with 1 ml of sterile artificial saliva (with 0.01% sucrose) and 1 ml of pooled saliva in a 24 well microplate. Freshly prepared treatment solutions were prepared for each of the composition of Table 1 comprising 1 part composition and 2 parts sterile distilled water. The treatment solutions were then added to the well and allowed to contact with the HAP disks for 10 mins. The treatment solutions were then replaced with 2 ml of sterile PBS and allowed to contact for 1 min. The liquid phase was then removed and replaced by 2 ml of sterile artificial saliva. The disks were treated in triplicates for each composition of Table 1 for 8 days. At intervals of 2, 4, and 8 days the disks were collected aseptically and transferred into half strength pre-reduced thioglycollate medium. 100 μl of the collected samples were plated in duplicates for each disk on Neomycin-Vancomycin (NV) Agar, for Total Gram negative Anaerobes. Plates were surface spread using a sterile spreader and incubated anaerobically@37° C. for 72 hours before counting the colonies. The pH was monitored for the entire period of the study using the liquid phase. The UoM number represents the log CFU/mL of bacterial in the sample. The lower the UoM number, the lower the bacterial concentration and the more effective the antibacterial efficacy of the oral care composition.

TABLE 2

| Sample | Oleanic Acid | Eugenol | UoM |
|---|---|---|---|
| Oral Care Composition #1 | 0.1% | 0.05% | 3.75 |
| Comparative Example A | 0.1% | — | 3.92 |
| Comparative Example B | — | 0.05% | 3.88 |
| Comparative Example C | 0.15% | 0.05% | 3.77 |

As illustrated in Table 2, the oral care composition including the mixture of antibacterial agents having a 2:1 ratio of oleanic acid to eugenol displayed enhanced antibacterial efficacy when compared to comparative compositions including oleanic acid or eugenol separately or including other ratios of oleanic acid to eugenol, such as 3:1 as in Comparative Composition C.

Accordingly, as illustrated in Table 2, Oral care compositions according to embodiments of the present disclosure provide enhanced antibacterial effects due to the synergistic effects of oleanic acid and eugenol when present at a 2:1 weight ratio. In other implementations, oleanic acid and eugenol are present at a weight ratio between 2:1 and 3:1.

The present disclosure has been described with reference to exemplary embodiments. Although a few embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

What is claimed is:

1. A method for increasing the antibacterial effect of an oral care composition, comprising:
adding a mixture of antibacterial agents to the oral care composition;
wherein the mixture of antibacterial agents consists of oleanic acid and eugenol;
wherein oleanic acid and eugenol are at a 2:1 weight ratio; and
wherein the oleanic acid is at 0.10 weight % based on the total weight of the oral care composition; and
wherein the eugenol is at 0.05 weight % based on the total weight of the oral care composition; and
wherein other than said mixture of antibacterial agents, the oral care composition lacks additional antibacterial agents.

2. The method of claim 1, wherein eugenol comprises one or more of eugenol, methyl eugenol, iso-eugenol, or mixtures thereof.

3. A method, for increasing the antibacterial effect of an oral care composition, comprising:

adding a mixture of antibacterial agents to the oral care composition;
wherein the mixture of antibacterial agents consists of oleanic acid and eugenol at a 3:1 weight ratio; and wherein the oleanic acid is at 0.15 weight % based on the total weight of the oral care composition; and
wherein the eugenol is at 0.05 weight % based on the total weight of the oral care composition; and
wherein other than said mixture of antibacterial agents, the oral care composition lacks additional antibacterial agents.

* * * * *